(12) United States Patent
Panescu (10) Patent No.: US 6,746,401 B2
(45) Date of Patent: Jun. 8, 2004

(54) TISSUE ABLATION VISUALIZATION

(75) Inventor: Dorin Panescu, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 72 days.

(21) Appl. No.: 10/139,994

(22) Filed: May 6, 2002

(65) Prior Publication Data

US 2003/0208123 A1 Nov. 6, 2003

(51) Int. Cl.$^7$ .................................................. A61B 8/00
(52) U.S. Cl. .................................. 600/439; 600/458
(58) Field of Search ................................ 600/443, 451, 600/458, 459, 454, 455, 456, 466, 467, 468, 439; 607/122

(56) References Cited

U.S. PATENT DOCUMENTS

| | | |
|---|---|---|
| 4,699,147 A | 10/1987 | Chilson et al. |
| 4,718,433 A | 1/1988 | Feinstein |
| 4,940,064 A | 7/1990 | Desai |
| 5,156,151 A | 10/1992 | Imran |
| 5,311,866 A | 5/1994 | Kagan et al. |
| 5,393,524 A | 2/1995 | Quay |
| 5,578,292 A | 11/1996 | Schneider et al. |
| 5,695,460 A * | 12/1997 | Siegel et al. .................. 604/21 |
| 5,704,361 A * | 1/1998 | Seward et al. ............... 600/466 |
| 5,752,518 A * | 5/1998 | McGee et al. ............... 600/463 |
| 5,876,345 A * | 3/1999 | Eaton et al. .................. 600/466 |
| 6,004,269 A * | 12/1999 | Crowley et al. ............. 600/439 |
| 6,171,246 B1 * | 1/2001 | Averkiou et al. ............ 600/458 |
| 2001/0007933 A1 | 7/2001 | Lesh et al. |
| 2001/0021371 A1 | 9/2001 | Eriksen et al. |

OTHER PUBLICATIONS

Lardo, et al; "Visualization and Temporal/Spatial Characterization of Cardiac Radiofrequency Ablation Lesions Using Magnetic Resonance Imaging" Circulation 200; 102:698–705.
Steiner, et al; "Monitoring of Radio Frequency Tissue Ablation in an Interventional Magnetic Resonance Enviroment", Investigative Radiology, 1997, vol. 32, No. 11, 671–678.
Saxon, et al; "Transesophageal Echocardiography During Radiofrequency Catheter Ablation of Ventricular Tachycardia" Am J Cardiol 1993; 72:658–661.
Ren, et al "Echocardiographic Lesion Characteristics Associated with Successful Ablation of Inappropriate Sinus Tachycardia"; J Cardiovasc Electrophysiol Jul. 2001; 12(7):814–8.
Sutherland, Fleming, McDicken case, Abstract of Italian Article, G Ital Cardiol May 1995; 25 (5): 639–47.

* cited by examiner

Primary Examiner—Francis J. Jaworski
(74) Attorney, Agent, or Firm—Bingham McCutchen LLP (57) ABSTRACT

Systems and methods for visualizing ablation lesions are provided. A contrast agent is injected into an artery that feeds blood to tissue surrounding an ablation lesion. During or after contrast agent injection, the ablation lesion and surrounding tissue is imaged using an imager that is responsive to the injected contrast agent. In one non-limiting embodiment, the contrast agent comprises echogenic particles, e.g., echogenic microbubbles, and the imager is an ultrasound imager.

16 Claims, 9 Drawing Sheets

TISSUE ABLATION VISUALIZATION

FIELD OF THE INVENTION

The invention relates generally to tissue ablation and more particularly to systems and methods for visualizing ablated tissue.

BACKGROUND OF THE INVENTION

In order for the heart to beat regularly and pump blood efficiently, special conductive tissues in the heart emit electrical pulses that conduct throughout the heart. As the electrical pulses conduct through the heart, they initiate contractions of the heart muscles (i.e., myocardium) causing the heart muscles to contract in an orderly sequence. Diseased heart tissue may disrupt the normal conduction of the electrical impulses and/or produce abnormal electrical activity in the heart, resulting in cardiac arrhythmia. For example, diseased heart tissue may cause electrical pulses to cycle repeatedly within a local region of the heart, inducing sustained twitching of the heart.

Cardiac arrhythmia is commonly treated using a steerable electrophysiological ("EP") catheter that may be precisely positioned anywhere in the heart. The EP catheter is generally used during two distinct phases of treatment for the arrhythmia. In one phase of treatment, the catheter is used to map the electrical activity of the heart in order to identify and locate the source and/or pathway of the abnormal electrical activity associated with the arrhythmia. This procedure is commonly referred to as "mapping". During the other phase of treatment, the same catheter is used to create an ablation lesion at the site where the diseased heart tissue has been located. This procedure is commonly referred to as "ablation".

Ablation procedures using EP catheters are typically performed using radio frequency ("RF") energy. In this regard, an EP catheter has one or more ablation electrode(s) located at its distal end. In order to create an ablation lesion at a targeted site, the EP catheter is steered within the heart to position the ablation electrode(s) at the targeted site. Typically, the ablation electrode(s) are placed in contact with the endocardium (inner heart wall) of the targeted site. The ablation electrode(s) then applies RF energy to the targeted site. The applied RF energy causes resistance heating of the tissue adjacent to the ablation electrode(s), producing an ablation lesion at the targeted site.

Successful treatment of cardiac arrhythmia requires that the ablation lesion have a sufficient extent and depth in the myocardium (heart muscle) to effectively eliminate the source and/or pathway of the abnormal electrical activity associated with the arrhythmia. Therefore, systems and methods for visualizing the extent and/or depth of ablation lesions would be highly desirable.

SUMMARY OF THE INVENTION

The present inventions are directed to a method for visualizing an ablation lesion. The inventive method comprises injecting a contrast agent into an artery that feeds blood to live tissue surrounding the ablation lesion, and imaging the ablation lesion and the surrounding live tissue with an imager that is responsive to the contrast agent. By way of non-limiting example, the ablation lesion can be located under the endocardial surface of a heart, in which case, the artery can be a coronary artery that feeds live heart tissue. The contrast agent can comprise echogenic particles, e.g., microbubbles, which are typically small enough (e.g., less than 8 microns) to pass through capillaries, so that the open capillaries in the live tissue allow the contrast agent to perfuse therein, while the closed capillaries in the nonviable tissue of the ablation lesion prevent the contrast agent from perfusing therein. In the case of a contrast agent that comprises echogenic particles, the imager can take the form of an interior or exterior ultrasound imager. It should be emphasized, however, that although the preferred embodiment describes an echogenic-based contrast agent and an ultrasound imaging as its preferred means for imaging the ablation lesion, the present invention should not be so limited, and contemplates any contrast agent that is able to distinguish between live tissue and ablated tissue and any imager that is responsive to the contrast agent. For example, optical, MRI or CT imaging technologies may be used with an appropriate type of contrast enhancing agent.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
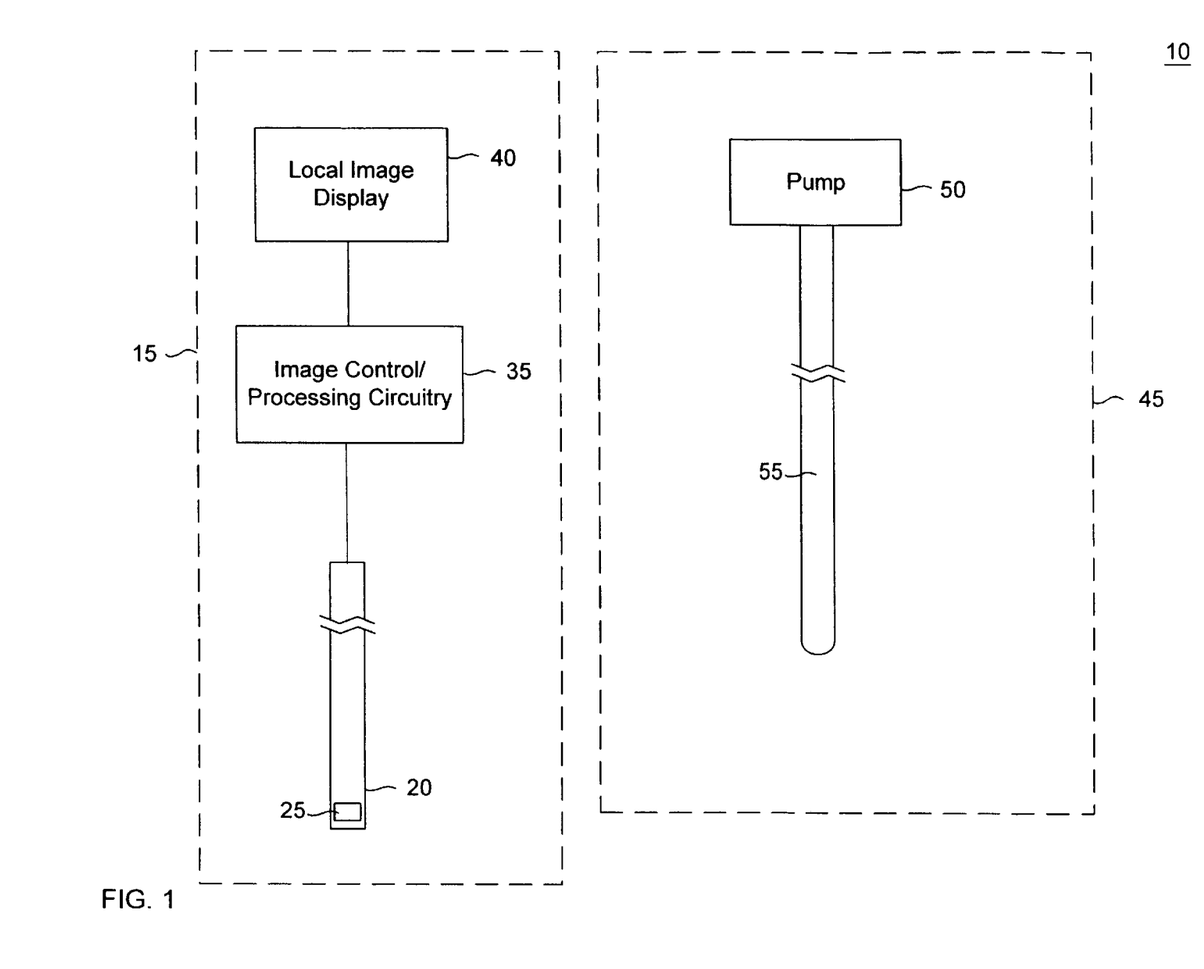
FIG. 1 illustrates the components of an ablation imaging system according to an embodiment of the invention.

FIG. 1 illustrates an exemplary ablation lesion visualization system 10 according to an embodiment of the invention for visualizing the extent and/or depth of an ablation lesion.

The ablation visualization system 10 generally comprises an injection subsystem 45 for injecting contrast agent into the body and an imaging subsystem 15 that is responsive to the contrast agent.

Figure 2:
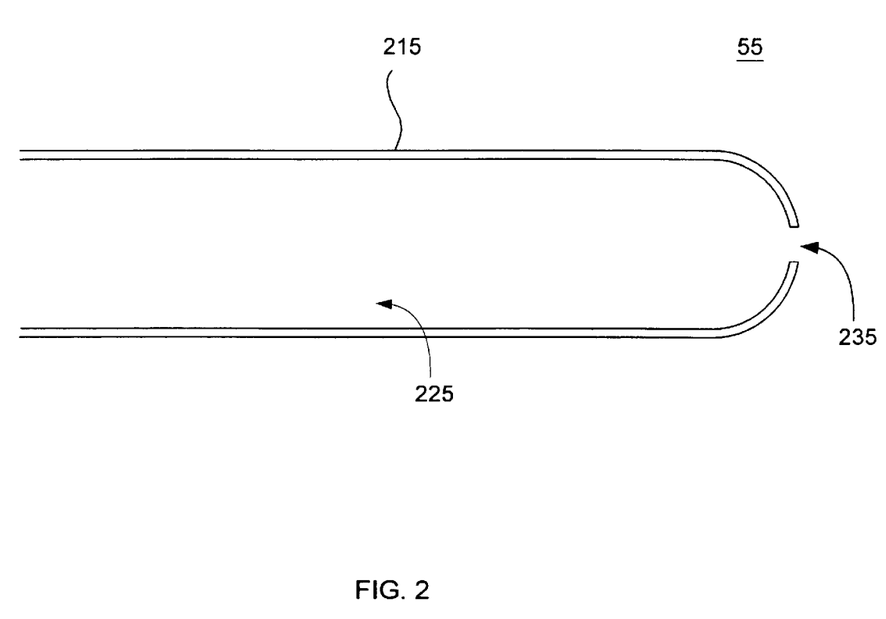
FIG. 2 illustrates a cross-sectional view of the distal end of an injection catheter used by the ablation lesion imaging system of FIG. 1.

The injection subsystem 45 comprises an injection catheter 55, and an infusion pump 50 fluidly coupled to the proximal end of the catheter 55. The injection catheter 55 is constructed for insertion into a blood vessel (e.g., an artery) and is preferably made of a flexible material so that it can bend along the tortuous path of the blood vessel. Referring to FIG. 2, the injection catheter 55 comprises a catheter body 215 having a lumen 225 extending therethrough, and an opening 235 at its distal tip. The lumen 225 fluidly couples the pump 50 (not shown in FIG. 2) to the opening 235 at the distal tip of the catheter body 215. Alternatively, the opening 235 may be located on the side of the catheter body 215 near the distal tip.

It is to be understood that the injection catheter 55 described above is merely illustrative and that the invention may use any one of a number of injection catheters known in the art for injecting diagnostic and/or therapeutic agents into a blood vessel. For example, injection catheters commonly used in "angiography" procedures for visualizing blood vessel structures in a fluoroscopic image with radiopaque dye can be used. These injection catheters typically have an outer diameter of 3–4 French.

Referring back to FIG. 1, the imaging subsystem 15 comprises a peripheral imaging device 20, image control/processing circuitry 35 coupled to the imaging device 20, and an image display 40 coupled to the image control/processing circuitry 35. The imaging device 20 may be constructed for insertion into the body, e.g., a catheter, to image the interior of the body. Alternatively, the imaging device 20 may be an external imaging device that images the interior of the body from a position outside the body. The imaging device 20 comprises an imaging element 25, e.g., a rotating ultrasound imager, a phased array ultrasound imager, or the like. The imaging element 25 produces signals, e.g., electrical signals, representing the interior of the body and outputs these signals to the image control/processing circuitry 35. The image control/processing circuitry 35 processes these signals into local interior images of the body and displays the interior images on the image display 40.

Figure 3:
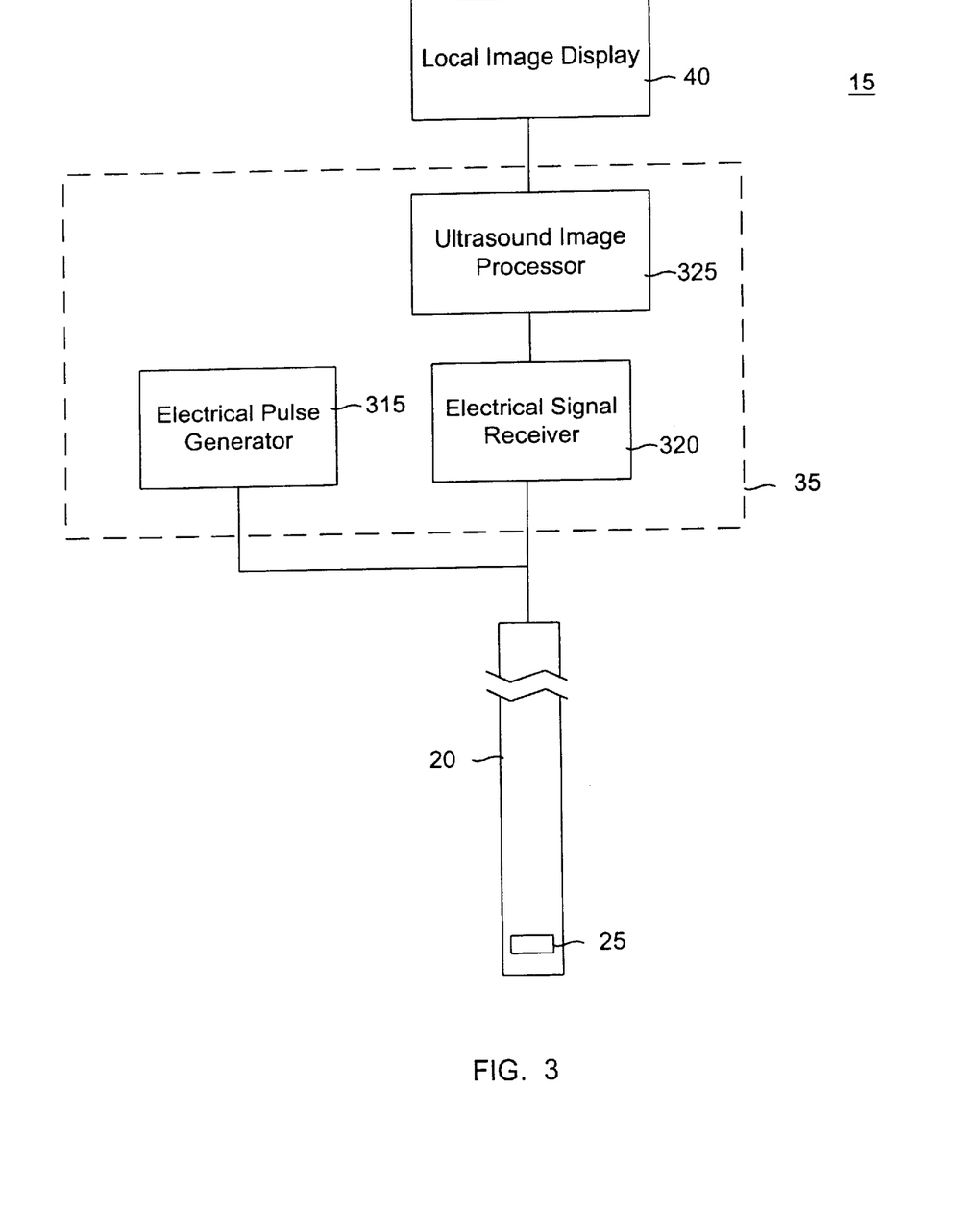
FIG. 3 illustrates an ultrasound imaging subsystem used by the ablation lesion imaging system of FIG. 1.

FIG. 3 illustrates an ultrasound-based local imaging subsystem 15 according to one embodiment of the invention, in which the imaging device 20 takes the form of an ultrasound imaging device 20 and the imaging element(s) 25 takes the form of one or more ultrasound transducer(s) 25. The ultrasound transducer(s) 25 may be rotated within the imaging device 20 by a drive shaft coupled to a drive motor (not shown) in order to obtain cross-sectional images (i.e. "slices") of the body. Alternatively, the ultrasound transducer(s) 25 may be arranged in a one-or-two dimensional phased array on the imaging device 20 for imaging a plane and/or sector of the body. The image control/processing circuitry 35 further includes an electrical pulse generator 315 and an electrical signal receiver 320, both of which are coupled to the ultrasound transducer(s) 25. The ultrasound image control/processing circuitry 35 further includes an ultrasound image processor 330 coupled to the electrical signal receiver 220.

To obtain an ultrasound image of the interior of the body, the imaging device 20 may be inserted into the body or placed on the skin surface of the body with the ultrasound transducer(s) 25 directed towards the interior of the body. The pulse generator 315 transmits electrical pulses to excite the ultrasound transducer(s) 25. The transducer(s) 25 convert the electrical pulses into pulses of ultrasound energy, which are emitted in the body. A portion of the ultrasound energy is reflected off of the internal anatomy of the body back to the transducer(s) 25. The transducer(s) 25 convert the back-reflected ultrasound energy into electrical signals representing the interior of the body. The electrical signals are detected by the electrical signal receiver 320 and outputted to the ultrasound image processor 330, which processes the received electrical signals into an ultrasound image of the body using known ultrasound image processing methods. The electrical signal receiver 320 may amplify and/or filter the electrical signals before outputting them to the ultrasound image processor 330. The ultrasound image processor 330 displays the ultrasound image on the image display 40.

A three-dimensional ultrasound image may be obtained from an ultrasound imaging device 20 that is only capable of imaging two-dimensional cross-sections of the body. This is done by having the ultrasound imaging device 20 sequentially image different cross-sections of the body and aggregating (i.e., piecing together) the cross-sectional images of the body to construct a 3-D image of the body. The ultrasound imaging device 20 may image the different cross-sections of the body by mechanically moving the transducer 25 to different locations within the body and obtaining cross-sectional images at the different locations.

Figure 4:
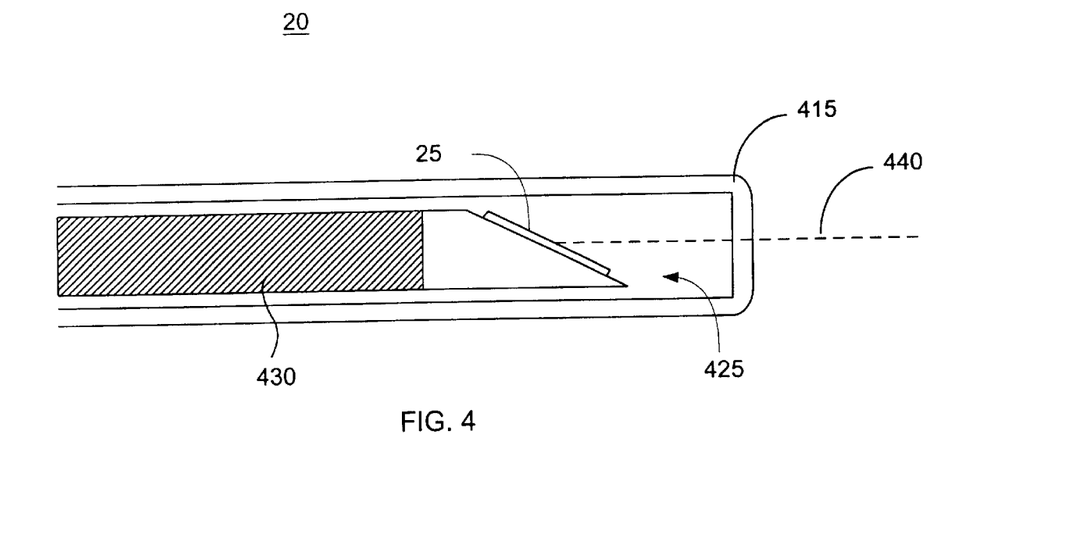
FIG. 4 illustrates a cross-sectional view of an ultrasound imaging catheter used in the ultrasound imaging subsystem of FIG. 3.

FIG. 4 illustrates a cross-sectional view of an embodiment of an ultrasonic imaging catheter 20, in which the ultrasound transducer(s) 25 takes the form of a rotating ultrasound imaging transducer 25. The imaging catheter 20 comprises an elongated catheter body or sheath 415 having a lumen 425 extending therethrough. The catheter body 415 is made of a flexible material so that it is able to bend along the path of a body lumen. The imaging device 20 further includes a drive shaft 430 extending through the lumen 425. The rotating ultrasound imaging transducer 25 is mounted on the distal end of the drive shaft 430. The catheter body 415 includes a clear acoustic window (not shown) for allowing ultrasound pulses to pass through the catheter body 415. The lumen 425 may be filled with fluid, e.g., water, to better couple ultrasound energy from the ultrasound transducer 25 to the surrounding body. An example of this type of imaging catheter is the 9-F (French) 9-MHz Intracardiac Echocardiography "ICE" catheter commercialized by Boston Scientific.

To obtain an interior cross-sectional image of the body, the imaging transducer 25 is mechanically rotated one revolution (360 degrees) along its axis 440 while simultaneously emitting ultrasound pulses at different angular directions in the body. The ultrasound image processor 330 processes the electrical signals received during one revolution of the ultrasound transducer 25 to construct the cross-sectional image of the body. The local imaging subsystem 35 may continuously update the ultrasound image to provide a real-time image of the body.

To obtain a three-dimensional image of a body volume, the ultrasound transducer 25 may be displaced axially within the catheter body 415 by, e.g., pulling back the drive shaft 430. As the transducer 25 is displaced axially, the ultrasound transducer 25 is rotated to obtain multiple cross-sectional images (i.e., "slices") of the body at different positions within the body. The ultrasound image processor 330 then aggregates (i.e., pieces together) the multiple cross-sectional images to reconstruct the volume of the body using known volume reconstruction methods. Further details on this 3-D imaging technique can be found in U.S. Pat. No. 5,724,978 to Tenhoff entitled "Enhanced accuracy of three-dimensional intraluminal ultrasound (ILUS) image reconstruction," which is fully and expressly incorporated herein by reference.

Before producing and visualizing an ablation lesion in the heart, the physician must first locate the source and/or pathway within a heart chamber causing arrhythmia. Typically, the physician does this by mapping the electrical activity of the heart camber using, e.g., an EP catheter equipped with mapping electrodes and location sensors, as is known in the art. The physician then examines the map of the electrical activity of the heart chamber on a display to identify and locate the source and/or pathway of the arrhythmia. The EP catheter may also be equipped with pacing electrodes for inducing arrhythmia during the mapping procedure to ensure that the abnormal electrical activity associated with the arrhythmia is shown on the map of the electrical activity of the heart chamber.

During the ablation procedure, an ablation lesion is created at a targeted site where the source and/or pathway of the arrhythmia has been located. The ablation lesion may be created by heating the tissue at the targeted site by applying RF energy, laser energy, and/or direct current to the tissue. For example, the EP catheter used to map the electrical activity of the heart may include one or more ablation electrodes for applying RF energy to the targeted site. The ablation lesion may also be created by injecting a chemical (e.g., ethanol) and/or cryogenic fluid into the tissue at the targeted site.

The tissue in the ablation lesion is characterized by necrosis (i.e., dead tissue). In addition, the capillaries in the ablation lesion are closed, stopping blood flow to the tissue in the ablation lesion. The ablation lesion may be a focal or a linear ablation lesion. A focal ablation lesion is localized around a focal point, and a linear ablation lesion extends (e.g., a few centimeters) along a line. A linear lesion may be created, e.g., by dragging an ablation electrode along the heart wall, creating several closely spaced lesions and/or using a long ablation electrode.

Figure 5:
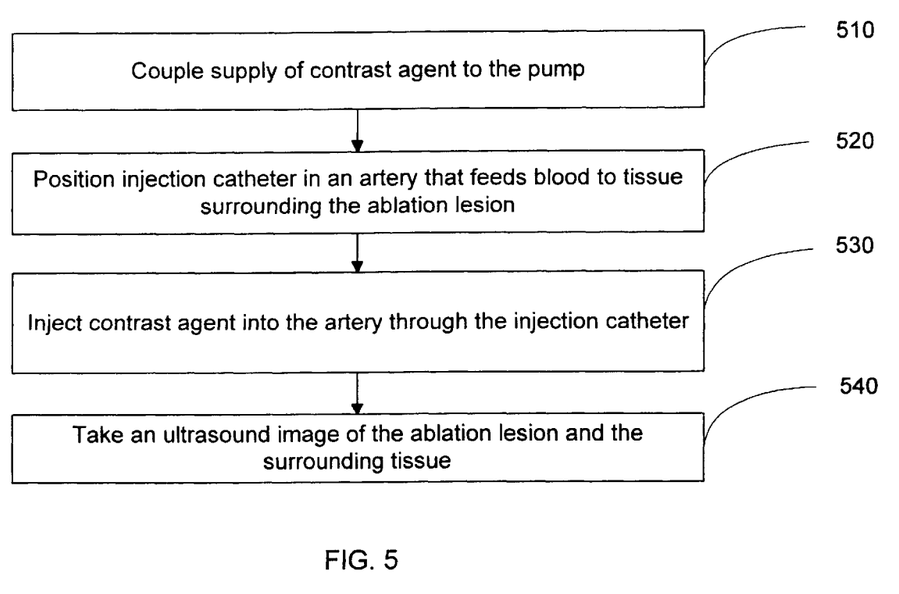
FIG. 5 is a flowchart illustrating an ablation lesion visualization method that may be performed by the ablation imaging system of FIG. 1.

A method for visualizing the ablation lesion according to an embodiment of the invention will now be described with reference to FIG. 5.

In step 510, a supply of contrast agent is fluidly coupled to the infusion pump 50, e.g., from a syringe containing the contrast agent. In one embodiment of the invention, the contrast agent contains echogenic particles in a solution. Preferably, the echogenic particles are made of a material that reflects ultrasound waves such as albumine-based compounds. For example, the material may reflect ultrasound waves in the body by having a higher density than blood and body tissue. The echogenic particles are each comparable in size to a red blood cell (a few microns) so that they can pass through the capillary structures of the body without causing blockage. The echogenic particles may take the form of microbubbles with each microbubble, preferably, having a diameter of less than 8 microns. Examples of suitable contrast agents containing echogenic microbubbles include OPTISON and ALBUMEX.

In step 520, the distal tip of the injection catheter 55 is positioned in a coronary artery that feeds blood to the tissue surrounding the ablation lesion. The injection catheter 55 may be guided in the artery using fluoroscopy, e.g., by placing a radiopaque marker on the distal tip of the catheter 55 for identifying the location of the distal tip in a fluoroscopic image.

Figure 6:
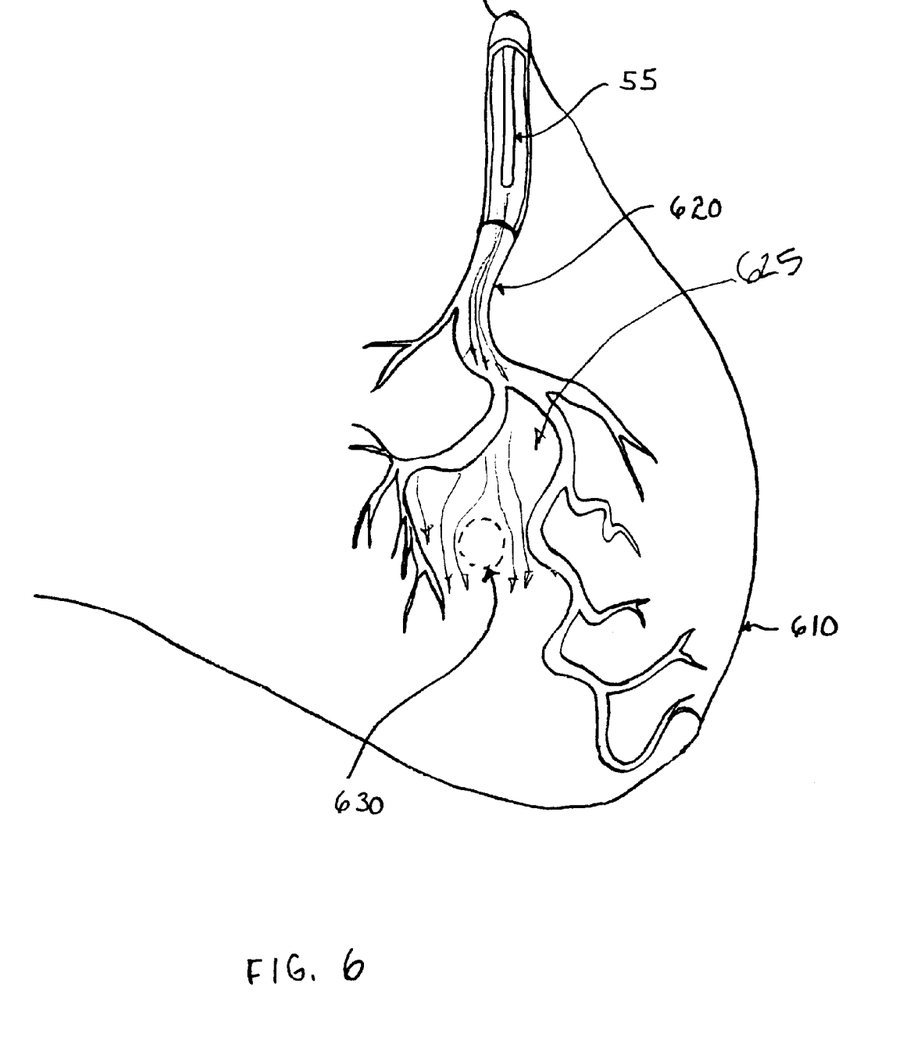
FIG. 6 illustrates the placement of an injection catheter in a patient's coronary artery in accordance with a step of the method of FIG. 5.

An example of step 520 is illustrated in FIG. 6, in which the injection catheter 55 is positioned in the left coronary artery 620. A section of the left coronary artery 620 is cutaway in FIG. 6 to reveal the injection catheter 55. In this illustrative example, a focal ablation lesion 630 (shown in dashes) is created in the interior of the left ventricle 610 wall. The left coronary artery 620 branches off into branches that feed blood to the heart tissue 625 surrounding the ablation lesion 630 in the left ventricle 610.

Referring back to FIG. 5, in step 530, the contrast agent is injected into the coronary artery through the opening 235 of the injection catheter 55. This is done by having the infusion pump 50 pump the contrast agent into the catheter lumen 225 at an injection rate of, e.g., a few milligrams per minute. From the coronary artery, the echogenic particles of the contrast agent (shown as arrows in FIG. 6) perfuse into the live tissue 625 surrounding the ablation lesion. Because of their small size, the particles are able to pass through the capillaries of the live tissue 625, and therefore perfuse throughout the live heart tissue 625. The echogenic particles, however, do not perfuse into the dead tissue of the ablation lesion 630 because of its closed capillaries.

In step 540, during or after contrast agent injection, an ultrasound image is taken of the ablation lesion 630 and surrounding tissue 625 using the ultrasound imaging device 20. The ultrasound image may be taken from inside the heart chamber, e.g., by positioning an ultrasound imaging catheter 20 within the heart chamber. The ultrasound image may also be taken from the outside the body, e.g., by directing the ultrasound transducer(s) of an external ultrasound imaging device 20 towards the heart chamber.

Because of the perfusion of the echogenic particles into the live tissue 625 surrounding the ablation lesion 620, the live tissue 625 reflects more of the ultrasound waves emitted from the ultrasound imaging device 20 than the ablation lesion 630. This causes the surrounding live tissue 625 to appear brighter in the ultrasound image than the ablation lesion 630, thereby providing contrast between the ablation lesion 630 and the surrounding live tissue 625 in the ultrasound image. This contrast enables a physician to discern the ablation lesion 630 in the ultrasound image, and therefore ascertain the extent and/or depth of the ablation lesion 630 in the myocardium from the ultrasound image.

Figure 7:
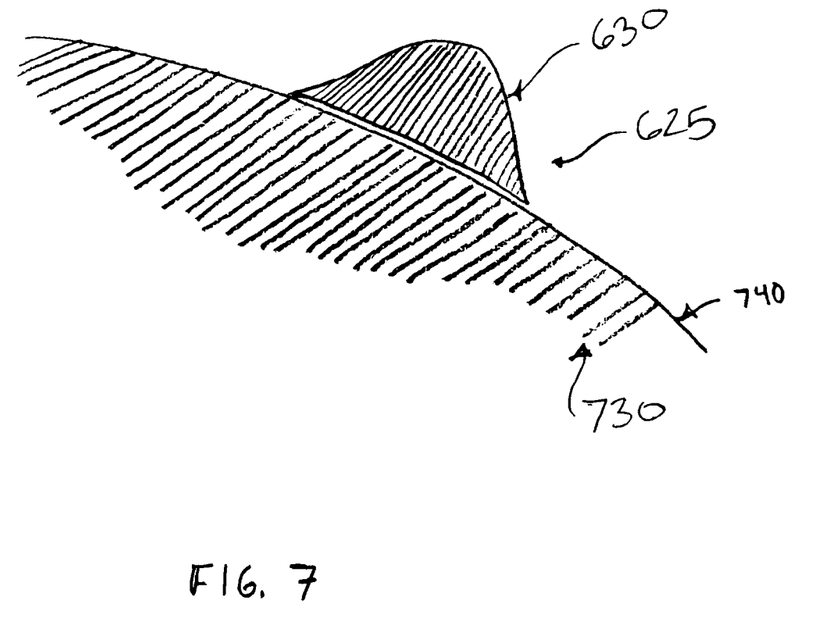
FIG. 7 illustrates an example of an ultrasound image of an ablation lesion obtained from the ablation lesion visualization method of FIG. 5.

An example of an ultrasound image obtained using the ablation visualization method is illustrated in FIG. 7. The ultrasound image shows a cross-section of a heart chamber containing the ablation lesion 630. In the ultrasound image, the ablation lesion 630 appears as a dark region, while the live tissue 625 in the heart chamber wall 740 surrounding the ablation lesion 630 appears as a white region due to the presence of echogenic particles in the live tissue 625. The dark region of the ablation lesion 630 is located within the white region of the surrounding live tissue 625. The interior volume 730 of the heart chamber may appear as a dark region (shown in FIG. 7) or a bright region, depending on the amount of time lapsed since the injection of the contrast agent. The contrast agent will ultimately arrive inside the chamber, thereby brighten it up, as explained further below.

The ablation visualization method may be used to provide a physician with valuable feedback on the extent and/or depth of an ablation lesion during an ablation procedure. For example, the physician may create an ablation lesion at a targeted site, and use the ablation visualization method to measure the extent and/or depth of the ablation lesion. Based on this measurement, the physician may determine whether the ablation lesion has sufficient extent and/or depth to treat the arrhythmia or further ablation is needed. The physician may repeat ablation followed by ablation visualization a number of times until he or she determines that the ablation has reached sufficient extent and/or depth to treat the arrhythmia.

Visualization of the ablation lesion requires that the contrast between the ablation lesion and surrounding live tissue in the ultrasound image be high enough to distinguish between the ablation lesion and the surrounding live tissue. The contrast level depends of the amount of echogenic particles present in the live tissue during ultrasound imaging. The amount of echogenic particles in the live tissue is affected by the contrast agent injection rate and the perfusion rate of the live tissue. The injection rate determines the rate at which the particles enter the capillaries of the surrounding live tissue, while the perfusion rate determines the rate at which the particles exits the capillaries of the surrounding live tissue to the rest of the circulatory system. The perfusion rate varies from patient to patient, and depends on such factors as the health of the patient, the age of the patient, and the like. As a result, a physician may not initially know the injection rate needed to provide a sufficient amount of echogenic particles in the surrounding live tissue to obtain adequate contrast between the ablation lesion and the surrounding live tissue in the ultrasound image. In this case, the physician may begin with an initial injection rate, and increase the injection rate when there is not enough contrast for him or her to distinguish between the ablation lesion and the surrounding live tissue in the ultrasound image. The physician may continue to increase the injection rate until he or she observes adequate contrast.

In some cases, tissue ablation produces charred tissue by causing overheating of the tissue during ablation. In RF ablation, for example, the charred tissue is typically superficial, being localized on the surface of the ablation lesion. Charred tissue has a higher density than non-charred tissue due to the absence of water in the charred tissue. As a result, charred tissue reflects ultrasound waves, and therefore appears bright in an ultrasound image. Because charred tissue appears bright in an ultrasound image, the ablation visualization method may provide little or no contrast between the charred tissue in an ablation lesion and the surrounding live tissue. Fortunately, the charred tissue in an ablation lesion is typically localized on the surface of he ablation lesion with the underlying tissue in the ablation lesion being non-charred. In this case, a physician may still be able to ascertain the extent and/or depth of the ablation lesion in the myocardium by visualizing the underlying non-charred tissue of the ablation lesion.

Figure 8:
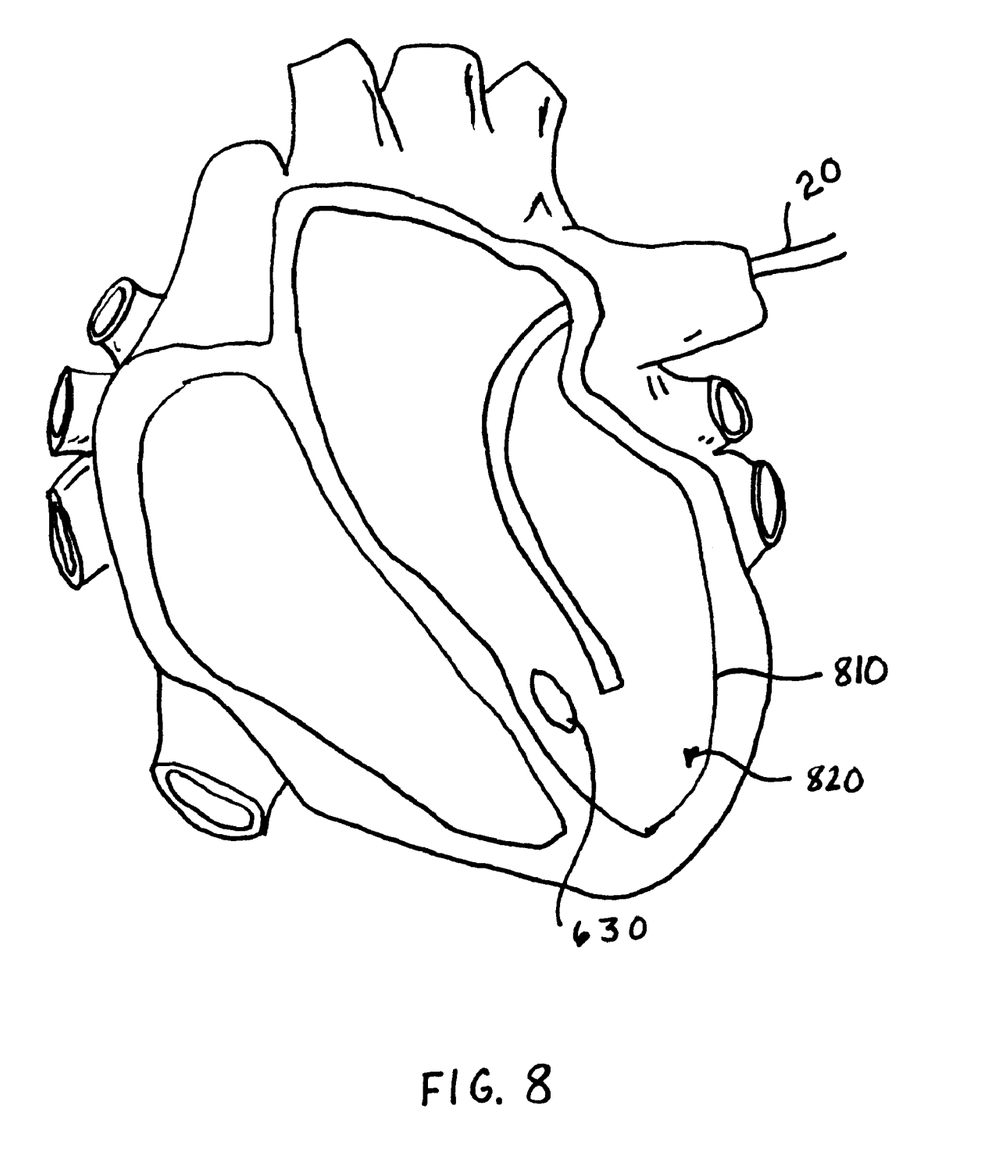
FIG. 8 illustrates the placement of an ultrasound imaging catheter within a patient's heart chamber in accordance with an imaging step of the method of FIG. 5.

FIG. 8 illustrates an embodiment, in which the ultrasound image in step 540 is taken from within the heart chamber 810 by positioning an ultrasound imaging catheter 20 within the heart chamber 810. The ultrasound transducer(s) of the imaging catheter 20 may take the form of a rotating transducer within the catheter body, a phased array of transducers disposed on the catheter body, or the like. The ultrasound imaging catheter 20 may be used to generate a 3-D ultrasound image of the ablation lesion 630. For example, using the ultrasound imaging catheter 20 of FIG. 4, the ultrasound transducer 25 may be pull-backed within the catheter body 415 along the length of the ablation lesion 630. As the transducer 25 is pulled-back, the ultrasound imaging catheter 20 obtains multiple cross-sectional images (i.e., slices) of the ablation lesion 630, which are aggregated (i.e., pieced together) to generate the 3-D image of the ablation lesion 630. An advantage of generating a 3-D ultrasound image of the ablation lesion 630 is that it visualizes the volume of the ablation lesion 630, allowing a physician to readily quantify both the extent and depth of the ablation lesion 630.

An issue that arises with imaging the ablation lesion 630 from within the heart chamber 810 is that the echogenic particles perfuse into the interior of the heart chamber 810 some time after the start of the contrast agent injection. When this occurs, the echogenic particles within the interior of the heart chamber 810 may reflect most or all of the ultrasound energy emitted from the ultrasound imaging catheter 20 before it reaches the ablation lesion 630. As a result, the ultrasound imaging catheter 20 will be unable to image the ablation lesion 630. In addition, the particles within the interior of the heart chamber 810 will cause the interior volume 820 of the heart chamber 810 to become white, thereby "whiting-out" the ultrasound image. When this occurs, the physician may decrease the injection rate of the contrast agent in order to decrease the amount of particles that perfuse into the interior volume of the heart chamber 810. A tradeoff of decreasing the injection rate, however, is that the contrast between the ablation lesion 630 and the surrounding tissue in the ultrasound image will be reduced. Alternatively or in addition, the physician may shorten the time interval of the ultrasound imaging so that the ultrasound imaging is completed before enough echogenic particles perfuse into the interior volume of the heart chamber 810 to "whiten-out" the ultrasound image.

Figure 9:
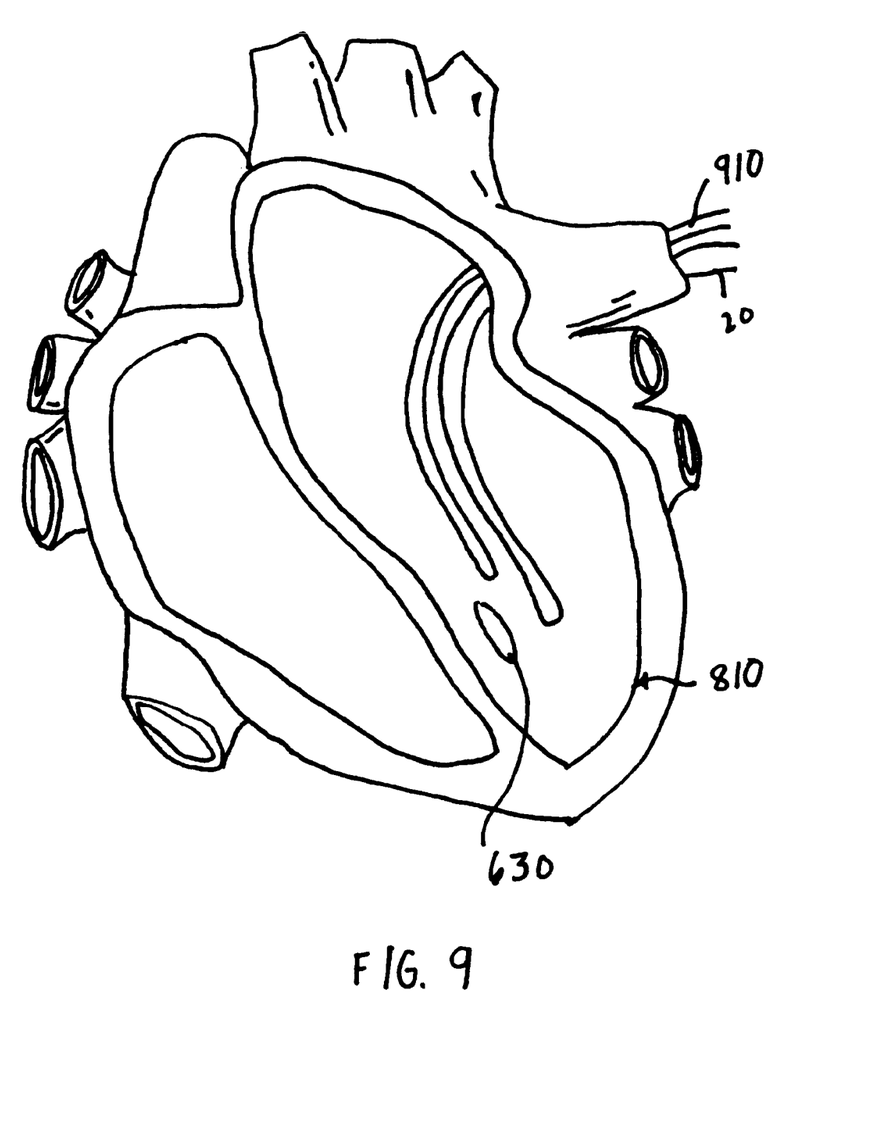
FIG. 9 illustrates the placement of an ultrasound imaging catheter and an ablation catheter within a patient's heart chamber in accordance with an imaging step of the method of FIG. 5.

The ablation catheter used in creating the ablation lesion may be left within the heart chamber 810 during ablation visualization. An example of this is illustrated in FIG. 9, in which the ablation catheter 910 is left in the heart chamber 810 as the ultrasound imaging catheter 20 images the ablation lesion 630. To prevent the ablation catheter 910 from obstructing the ultrasound image of the ablation lesion 630, the ablation catheter 910 may be positioned away from the ablation lesion 630 during ultrasound imaging. An advantage of leaving the ablation catheter 910 within the heart chamber 910 is that it makes it easier for a physician to perform further ablation, when necessary, after ablation visualization.

Tracking systems are commonly employed to track the position and/or orientation of catheters (e.g., ablation catheters) and/or their functional elements (e.g., ablation electrode, mapping electrodes) within a three-dimensional (3-D) coordinate system. These tracking systems typically comprise location sensors (e.g., ultrasound transducers) placed on the catheter being tracked, and a reference device that establishes the 3-D coordinate system. Details of an ultrasound-type tracking system can be found in patent application Ser. No. 09/128,304 to Willis et al. entitled "A dynamically alterable three-dimensional graphical model of a body region," which is fully and expressly incorporated herein by reference. Also, details of a magnetic-type of tracking system can be found in U.S. Pat. No. 5,391,199 to Ben-Haim, entitled "Apparatus and Method for Treating Cardiac Arrhythmias," which is fully and expressly incorporated herein by reference.

In one embodiment of the invention, the ultrasound image of the ablation lesion is registered (i.e., aligned) with the 3-D coordinate system of a tracking system. To do this, a catheter (e.g., ablation catheter) whose position is tracked by the tracking system is left within the heart chamber. An ultrasound image is then taken of both the ablation lesion and a portion of the catheter and/or its functional elements. The ultrasound image is then registered with the 3-D coordinate system by correlating the position of the catheter and/or its functional elements within the ultrasound image with the position of the catheter and/or its functional elements obtained from the tracking system.

The ultrasound image of the ablation lesion may also be registered with the 3-D coordinate system of a tracking system by tracking the position of the ultrasound imaging device 20 within the 3-D coordinate system. This may be done, e.g., by placing location sensors on the ultrasound imaging device 20 that are compatible with the tracking system and using the tracking system to track the position of the ultrasound imaging device 20 within the 3-D coordinate system during ultrasound imaging. The ultrasound image may then be registered (i.e., aligned) within the 3-D coordinate system by correlating the position of the ultrasound imaging device 20 relative to the ultrasound image with the position of the ultrasound imaging device 20 obtained from the tracking system.

In the foregoing specification, the invention has been described with reference to a specific embodiment thereof. It will, however, be evident that various modifications and changes may be made thereto without departing from the broader spirit and scope of the invention. For example, the invention is not limited to visualizing ablation lesions in the heart and may be used to visualize ablation lesions in other parts of the body. As another example, features known to those of skill in the art can be added to the embodiment. Other processing steps known to those of ordinary skill in the art may similarly be incorporated as desired. Additionally and obviously, features may be added or subtracted as desired. Accordingly, the invention is not to be restricted except in light of the attached claims and their equivalents.

What is claimed is:

1. A method for visualizing an ablation lesion, comprising:
   injecting a contrast agent into an artery that feeds blood to live tissue surrounding the ablation lesion;
   positioning an imager responsive to the contrast agent within a space adjacent the live tissue;
   imaging the ablation lesion and the surrounding live tissue with the imager; and
   minimizing the perfusion rate of the contrast agent from live tissue into the space to prevent interference of the imaging.

2. The method of claim 1, wherein the ablation lesion is located in the heart and the space is a heart chamber.

3. The method of claim 1, wherein the step of injecting the contrast agent into the artery comprises:
   positioning an injection catheter in the artery; and
   injecting the contrast agent into the artery through the injection catheter.

4. The method of claim 1, wherein the imaging step comprises:
   imaging multiple cross sections of the ablation lesion and the surrounding tissue; and
   aggregating the multiple cross-sectional images to generate a three-dimensional image of the ablation lesion and the surrounding tissue.

5. The method of claim 1, further comprising:
   registering the image of the ablation lesion and the surrounding tissue with a three-dimensional coordinate system.

6. The method of claim 1, further comprising:
   increasing the injection rate of the contrast agent in the injection step when the image of the ablation lesion and the surrounding tissue lacks sufficient contrast to distinguish between the ablation lesion and the surrounding tissue in the image.

7. The method of claim 1, further comprising:
   decreasing the injection rate of the contrast agent in the injection step when perfusion of the contrast agent into the space interferes with the imaging.

8. A method for visualizing an ablation lesion, comprising:
   injecting a contrast agent into an artery that feeds blood to live tissue surrounding the ablation lesion, wherein the contrast agent comprises echogenic particles;
   positioning an ultrasound imager responsive to the contrast agent within a space adjacent the live tissue;
   imaging the ablation lesion and the surrounding live tissue with an ultrasound imager; and
   minimizing the perfusion rate of the contrast agent from the live tissue into the space to prevent whiting out of the imaging.

9. The method of claim 8, wherein the echogenic particles are microbubbles.

10. The method of claim 9, wherein each microbubble has a diameter of less than 8 microns.

11. The method of claim 8, wherein the ablation lesion is located in the heart and the space is a heart chamber.

12. The method of claim 8, wherein the imaging step comprises:
    imaging multiple cross sections of the ablation lesion and the surrounding tissue; and
    aggregating the multiple cross-sectional images to generate a three-dimensional image of the ablation lesion and the surrounding tissue.

13. The method of claim 12, wherein the step of imaging the multiple cross section comprises:
    pulling back a ultrasound transducer within the ultrasound imager.

14. The method of claim 8, further comprising:
    registering the image of the ablation lesion and the surrounding tissue with a three-dimensional coordinate system.

15. The method of claim further comprising:
    increasing the injection rate of the contrast agent in the injection step when the image of the ablation lesion and the surrounding tissue lacks sufficient contrast to distinguish between the ablation lesion and the surrounding tissue in the image.

16. The method of claim 8, further comprising:
    decreasing the injection rate of the contrast agent in the injection step when perfusion of the contrast agent into the space whites out the imaging.

* * * * *